United States Patent [19]

Kluth et al.

[11] Patent Number: 4,832,733
[45] Date of Patent: May 23, 1989

[54] 3-AMINO-2-CYANO-ACRYLIC ACID ESTER HERBICIDES

[75] Inventors: Joachim Kluth, Langenfeld; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 35,547

[22] Filed: Apr. 3, 1987

[30] Foreign Application Priority Data

Apr. 17, 1986 [DE] Fed. Rep. of Germany ....... 3612941
Nov. 8, 1986 [DE] Fed. Rep. of Germany ....... 3638151

[51] Int. Cl.$^4$ .................. A01N 31/02; C07C 121/453
[52] U.S. Cl. ......................................... 71/98; 558/390; 558/303; 558/400
[58] Field of Search ............................ 558/390; 71/98

[56] References Cited

U.S. PATENT DOCUMENTS 3,406,183 10/1968 Real Laliherte .................. 558/390
4,154,599 5/1979 Hedrich ............................ 558/390
4,201,569 5/1980 Hedrich ............................ 558/390

OTHER PUBLICATIONS

Chemische Berichte 95.Jahrg./1962/No. 12, S.2831–3134 Rudolf Gompper and Werner Topfl; Carbonsaurederivate, V$^1$ Substituiert Dithiocarbonsauren and Ketenmercaptale$^{2,3}$; pp. 2862–2870.

Primary Examiner—Mary C. Lee
Assistant Examiner—J. Richter
Attorney, Agent, or Firm—Sprung Horn Kramer & Woods

[57] ABSTRACT

Herbicidally active 3-amino-2-cyano-acrylic acid esters of the formula

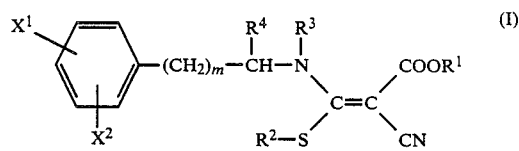

in which
$R^1$ represents alkoxyalkyl or benzyloxyalkyl
$R^2$ represents alkyl or alkenyl,
$R^3$ represents hydrogen or alkyl,
$R^4$ represents hydrogen, or represents alkyl which is optionally substituted by hydroxyl, halogen, alkoxy or dialkylamino,
$X^1$ and $X^2$ are identical or different and represent hydrogen, halogen, nitro, alkyl, alkoxy, alkylthio, halogenoalkyl, halogenoalkoxy, amino, alkylamino, alkylcarbonylamino, N-alkylcarbonyl-N-alkylamino, dialkylaminocarbonylamino or in each case optionally substituted aryl or aryloxy, or
$X^1$ and $X^2$ together with the adjacent phenyl radical represent naphthyl and
m represents the number 0, 1, 2, 3, 4 or 5.

Intermediates of the formula

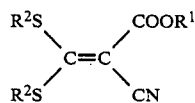

are also new.

12 Claims, No Drawings

3-AMINO-2-CYANO-ACRYLIC ACID ESTER HERBICIDES

The invention relates to new 3-amino-2-cyano-acrylic acid esters, a process for their preparation and their use as herbicides.

It is already known that certain aralkylaminoacrylonitriles have herbicidal properties (compare, for example, U.S. Pat. Nos. 4,154,599 and 4,201,569). Thus, for example, methyl 2-cyano-3-(1-phenylethylamino)-3-methyl-thioacrylate can be used for combating weeds. The action of this substance is good, but some weeds are not always completely affected when low amounts are applied, and also the selectivity is not always satisfactory.

New 3-amino-2-cyano-acrylic acid esters of the formula (I)

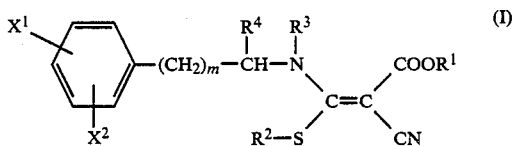

in which
$R^1$ represents alkoxyalkyl or benzyloxylalkyl,
$R^2$ represents alkyl or alkenyl,
$R^3$ represents hydrogen or alkyl,
$R^4$ represents hydrogen, or represents alkyl which is optionally substituted by hydroxyl, halogen, alkoxy or dialkylamino,
$X_1$ and $X_2$ are identical or different and represent hydrogen, halogen, nitro, alkyl, alkoxy, alkylthio, halogenoalkyl, halogenoalkoxy, amino, alkylamino, alkylcarbonylamino, N-alkylcarbonyl-N-alkylamino, dialkylaminocarbonylamino or in each case optionally substituted aryl or aryloxy, or
$X^1$ and $X^2$ together with the adjacent phenyl radical represent naphthyl and
m represents the number 0, 1, 2, 3, 4 or 5,
have now been found.

The 3-amino-2-cyano-acrylic acid esters of the formula (I) can exist in the E- or Z-form. They are chiefly obtained as mixtures of the two forms (E/Z).

In the case where $R^4$ does not represent hydrogen, the 3-amino-2-cyano-acrylic acid esters of the formula (I) contain at least one asymmetrically substituted carbon atom and can therefore exist in various enantiomeric forms. The invention relates both to the possible individual isomers and to mixtures of these isomers.

It has furthermore been found that the 3-amino-2-cyano-acrylic acid esters of the formula (I) are obtained by a process in which 2-cyano-acrylic acid esters of the formula (II)

in which $R^1$ and $R^2$ have the abovementioned meanings, are reacted with amines of the formula (III)

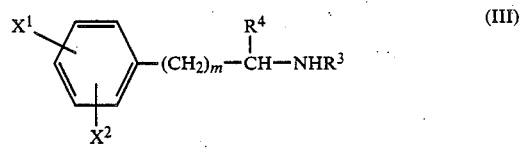

in which m, $X^1$, $X^2$, $R^3$ and $R^4$ have the abovementioned meanings,
if appropriate in the presence of diluents.

Finally, it has been found that the new 3-amino-2-cyano-acrylic acid esters of the formula (I) are distinguished by an outstanding herbicidal action.

Surprisingly, the 3-amino-2-cyano-acrylic acid esters of the formula (I) according to the invention have a considerably better herbicidal activity than methyl 2-cyano-3-(1-phenylethylamino)-3-methylthio-acrylate, which is a structurally similar active compound of the same type of action.

Formula (I) provides a general definition of the 3-amino-2-cyano-acrylic acid esters according to the invention. Preferred compounds of the formula (I) are those in which
$R^1$ represents alkoxyalkyl with in each case 1 to 6 carbon atoms in the individual alkyl parts, or represents benzyloxyalkyl with 1 to 6 carbon atoms in the alkyl part,
$R^2$ represents alkyl with 1 to 6 carbon atoms, or represents alkenyl with 3 to 8 carbon atoms,
$R^3$ represents hydrogen or alkyl with 1 to 6 carbon atoms,
$R^4$ represents hydrogen, or represents alkyl which has 1 to 6 carbon atoms and is optionally substituted by hydroxyl, fluorine, chlorine, $C_1$–$C_4$-alkoxy or di-$C_1$–$C_4$-alkylamino,
$X^1$ and $X^2$ are identical or different and represent hydrogen, fluorine, chlorine, bromine, nitro, $C_1$–$C_4$-alkyl, $C_1$–$C_4$-alkoxy, $C_1$–$C_4$-alkylthio, halogeno-$C_1$–$C_4$-alkyl or halogeno-$C_1$–$C_4$-alkoxy, amino, $C_1$–$C_4$-alkylamino, $C_1$–$C_4$-alkylcarbonylamino, N-$C_1$–$C_4$-alkylcarbonyl-N-$C_1$–$C_4$-alkylamino, Di-$C_1$–$C_4$-alkylamino-carbonylamino or represent aryl or aryloxy which have in each case 6 to 10 carbon atoms in the aryl part and are optionally monosubstituted, disubstituted or trisubstituted by identical or different substituents from the group comprising halogen, such as fluorine, chlorine and bromine, nitro, cyano, $C_1$–$C_2$-alkyl, $C_1$–$C_2$-alkoxy, $C_1$–$C_2$-alkylthio, trifluoromethyl, trifluoromethoxy and trifluoromethylthio or
$X^1$ and $X^2$ together with the adjacent phenyl radical represent naphthyl and
m represents the number 0, 1, 2 or 3.

Particularly preferred compounds of the formula (I) are those in which
$R^1$ represents alkoxyalkyl with in each case 1 to 4 carbon atoms in the individual alkyl parts or represents benzyloxyalkyl with 1 to 4 carbon atoms in the alkyl part,
$R^2$ represents alkyl with 1 to 4 carbon atoms or alkenyl with 3 to 6 carbon atoms,
$R^3$ represents hydrogen or alkyl with 1 to 4 carbon atoms,
$R^4$ represents hydrogen, or represents alkyl which has 1 to 4 carbon atoms and is optionally substituted by hydroxyl, fluorine, chlorine, methoxy, ethoxy, dimethylamino or diethylamino, $X^1$ and $X^2$ are identical or different and represent hydrogen, fluorine, chlorine, bromine, nitro, methyl, ethyl, methoxy, ethoxy, methylthio, ethylthio, trifluoromethyl, trifluoromethoxy, amino, methylamino, ethylamino, n-propylamino, i-propylamino, n-butylamino, tert.-butylamino, methylcarbonylamino, ethylcarbonylamino, n-propylcarbonylamino, i-propylcarbonylamino, n-butylcarbonylamino, i-butylcarbonylamino, tert.-butylcarbonylamino, N-methylcarbonyl-N-methylamino, N-ethylcarbonyl-N-methylamino, N-n-propylcarbonyl-N-methylamino, N-i-propylcarbonyl-N-methylamino, or represent phenyl or phenoxy which are optionally monosubstituted or disubstituted by identical or different substituents from the group comprising fluorine, chlorine, nitro, cyano, methyl, ethyl, methoxy, ethoxy, methylthio, ethylthio, trifluoromethyl, trifluormethoxy and trifluoromethylthio, or $X^1$ and $X^2$ together with the adjacent phenyl radical represent naphthyl and m represents the number 0, 1 or 2.

Especially preferred compounds of the formula (I) are those in which $R^1$ represents methoxyethyl, ethoxyethyl, n-propoxyethyl, i-propoxyethyl, n-butoxyethyl, i-butoxyethyl, sec.-butoxyethyl, benzyloxymethyl or benzyloxyethyl, $R^2$ represents methyl, ethyl, n-propyl, i-propyl, n-butyl, i-butyl or sec.-butyl, 1-propen-3-yl or 2-penten-4-yl, $R^3$ represents hydrogen, methyl, ethyl, n-propyl, i-propyl, n-butyl, i-butyl or sec.-butyl, $R^4$ represents hydrogen, methyl, ethyl, n-propyl, i-propyl, n-butyl, i-butyl or sec.-butyl, $X^1$ and $X^2$ are identical or different and represent hydrogen, fluorine, chlorine, nitro, methyl, methoxy, methylthio, trifluoromethyl, trifluoromethoxy, methylamino, ethylamino, methylcarbonylamino, ethylcarbonylamino or phenyl or phenoxy which are optionally monosubstituted or disubstituted by identical or different substituents from the group comprising fluorine, chlorine, nitro, cyano, methyl, methoxy, methylthio, trifluoromethyl, trifluoromethoxy and trifluoromethyl-thio, or $X^{1*}$ and $X^2$ together with the adjacent phenyl radical represent naphthyl and m represents the number 0 or 1.

The corresponding geometric and optical isomers of the compounds of the formula (I) are also preferred.

Particularly preferred optical isomers are the R- and S-enantiomers of the compounds of the formula (Ib)

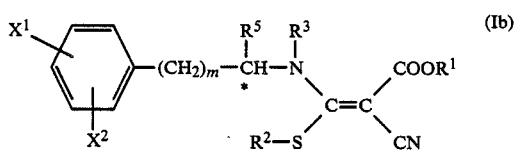

in which $X^1$, $X^2$, $R^1$, $R^2$, $R^3$ and m have the above-mentioned preferred meanings and in which the carbon atom labelled (*) and bonded to the nitrogen represents a chirality center, and $R^5$ represents $C_1$-$C_4$-alkyl.

Especially preferred compounds are the S-enantiomers of the compounds of the formula (Ib) in which $X^1$, $X^2$, $R^1$, $R^2$, $R^3$ and m have the above-mentioned particularly preferred meanings and $R^5$ represents methyl.

If methoxyethyl 2-cyano-3,3′-diethylthio-acrylate and 1-phenylethylamine are used as starting substances, the course of the process according to the invention can be represented by the following equation:

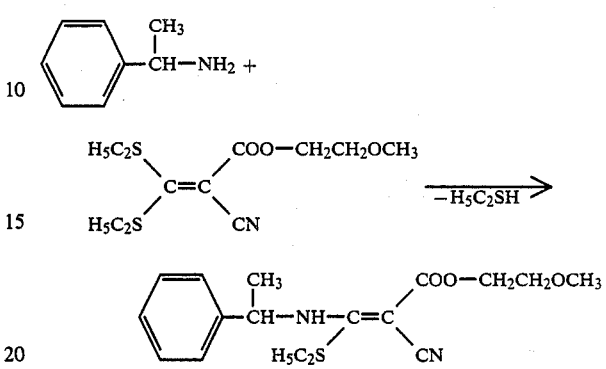

Formula (II) provides a general definition of the 2-cyano-acrylic acid esters to be used as starting substances in the process according to the invention. In formula (II), $R^1$ and $R^2$ preferably or in particular have the same meanings as are mentioned above as preferred or as particularly preferred in the context of the definition of the substituents for formula (I).

Examples which may be mentioned of the compounds of the formula (II) are:

TABLE 1

| $R^1$ | $R^2$ |
|---|---|
| —$CH_2CH_2OCH_3$ | $CH_3$ |
| —$CH_2CH_2OC_2H_5$ | $CH_3$ |
| —$CH_2CH_2OC_3H_7$—n | $CH_3$ |
| —$CH_2CH_2OC_3H_7$—i | $CH_3$ |
| —$CH_2CH_2OC_4H_9$—n | $CH_3$ |
| —$CH_2CH_2OC_4H_9$—i | $CH_3$ |
| —$CH_2CH_2OC_4H_9$—sec. | $CH_3$ |
| —$CH_2CH_2OC_4H_9$—tert. | $CH_3$ |
| —$CH_2CH_2OCH_3$ | $C_2H_5$ |
| —$CH_2CH_2OC_2H_5$ | $C_2H_5$ |
| —$CH_2\overset{\underset{\mid}{CH_3}}{CH}OC_2H_5$ | $C_2H_5$ |
| —$CH_2CH_2OC_3H_7$—n | $C_2H_5$ |
| —$CH_2CH_2OC_3H_7$—i | $C_2H_5$ |
| —$CH_2CH_2OCH_3$ | n-$C_3H_7$ |
| —$CH_2CH_2OC_2H_5$ | n-$C_3H_7$ |
| —$CH_2\overset{\underset{\mid}{CH_3}}{CH}OC_2H_5$ | n-$C_3H_7$ |
| —$CH_2CH_2OC_3H_7$—n | n-$C_3H_7$ |
| —$CH_2CH_2OC_3H_7$—i | n-$C_3H_7$ |
| —$CH_2CH_2OCH_3$ | i-$C_3H_7$ |
| —$CH_2CH_2OC_2H_5$ | i-$C_3H_7$ |
| —$CH_2\overset{\underset{\mid}{CH_3}}{CH}OC_2H_5$ | i-$C_3H_7$ |
| —$CH_2CH_2OC_3H_7$—n | i-$C_3H_7$ |
| —$CH_2CH_2OC_3H_7$—i | i-$C_3H_7$ |

TABLE 1-continued

| $R^1$ | $R^2$ |
|---|---|
| —CH₂CH₂OCH₂—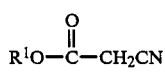 | CH₃ |
| —CH₂CH₂OCH₂—⟨⟩ | C₂H₅ |
| —CH₂CH₂OCH₂—⟨⟩ | n-C₃H₇ |
| —CH₂CH₂OCH₂—⟨⟩ | i-C₃H₇ |

The compounds of the formula (II) are new and can be prepared in a simple manner by known methods (compare Chem. Ber. 95 (1962), 2861-2869). The compounds of the formula (II) are obtained by a process in which 2-cyano-acetic acid esters of the formula (IV)

$$R^1O-\overset{O}{\underset{\|}{C}}-CH_2CN \quad (IV)$$

in which
$R^1$ has the abovementioned meanings,
are reacted with carbon disulphide in the presence of at least twice the molar amount of alkali metal alcoholate, such as, for example, NaOR¹, KOR¹ or sodium tert.-butanolate or potassium tert.-butanolate, and in the presence of inert diluents, such as, for example, diethyl ether, dioxane, tetrahydrofuran or alcohols of the formula R¹OH, at temperatures between −10° C. and +60° C., preferably between 0° C. and +40° C., to give the new salts of the formula (V)

$$\begin{array}{c}MS\\ \phantom{M}\diagdown\\ \phantom{MSM}C=C\\ \phantom{M}\diagup\phantom{MMM}\diagdown\\ MS\phantom{MMMM}COOR^1\end{array} \quad (V)$$

in which
$R^1$ has the abovementioned meanings and
M represents an alkali metal atom, and these compounds of the formula (V) are then reacted, if appropriate after being isolated, with alkylating agents of the formula (VI)

$$R^2Q \quad (VI)$$

in which
$R^2$ has the abovementioned meanings and
Q represents halogen, or represents the radical —OSO₂OR²,
in the presence of inert diluents, such as, for example, water, a water/acetone mixture or ethers, such as, for example, diethyl ether, di-n-butyl ether, tetrahydrofuran or dioxane, at temperatures between 0° C. and 80° C., preferably between +15° C. and +50° C.

Formula (IV) provides a general definition of the 2-cyanoacetic acid esters to be used for the preparation of the new compounds of the formula (II). In this formula (IV), $R^1$ preferably or particularly preferably represents those radicals which have already been mentioned as preferred or particularly preferred for this substituent in connection with the description of the substances of the formula (I) according to the invention.

The 2-cyanoacetic acid esters of the formula (IV) are known and/or can be prepared by known methods (compare, for example, WO Patent Specification No. 85/00598).

Examples which may be mentioned of the compounds of the formula (IV) are:

$$R^1O-\overset{O}{\underset{\|}{C}}-CH_2CN \quad (IV)$$

TABLE 2

| $R^1$ | $R^1$ | $R^1$ |
|---|---|---|
| —CH₂CH₂OCH₃ | —CH₂CH₂OC₄H₉—i | —CH₂CH₂CH₂—OCH₃ |
| —CH₂CH₂OC₂H₅ | —CH₂CH₂OC₄H₉—sec. | —CH₂CH₂CH₂—OC₂H₅ |
| —CH₂CH₂OC₃H₇—n | —CH₂CH₂OC₄H₉—tert. | —CH₂CH(CH₃)OCH₃ |
| —CH₂CH₂OC₃H₇—i | —CH₂CHOC₂H₅ (with CH₃ branch) | —CH₂CH₂OCH₂—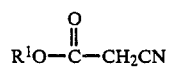 |
| —CH₂CH₂OC₄H₉—n | —CH₂CH₂OCH₂CH=CH₂ | |

Formula (V) provides a general definition of the salts also to be used as starting substances for the preparation of the new compounds of the formula (II). In this formula (V), $R^1$ preferably or particularly preferably represents those radicals which have already been mentioned as preferred or particularly preferred for this substituent in connection with the description of the substances of the formula (I) according to the invention. M in this formula represents an alkali metal atom, preferably a sodium or potassium atom.

The preparation of the new compounds of the formula (V) is carried out by the process described above.

Examples which may be mentioned of compounds of the formula (V) are:

$$\begin{array}{c}MS\phantom{MMM}CN\\ \phantom{M}\diagdown\phantom{M}|\\ \phantom{MMMM}C=C-COOR^1\\ \phantom{M}\diagup\\ MS\end{array} \quad (V)$$

M = sodium or potassium.

TABLE 3

| $R^1$ | $R^1$ | $R^1$ |
|---|---|---|
| $-CH_2CH_2OCH_3$ | $-CH_2CH_2OC_4H_9-i$ | $-CH_2CH_2CH_2-OCH_3$ |
| $-CH_2CH_2OC_2H_5$ | $-CH_2CH_2OC_4H_9-sec.$ | $-CH_2CH_2CH_2-OC_2H_5$ |
| $-CH_2CH_2OC_3H_7-n$ | $-CH_2CH_2OC_4H_9-tert.$ | $-CH_2CH(CH_3)OCH_3$ |
| $-CH_2CH_2OC_3H_7-i$ | $-CH_2\overset{\underset{\mid}{CH_3}}{CH}OC_2H_5$ | $-CH_2CH_2OCH_2-\phantom{x}$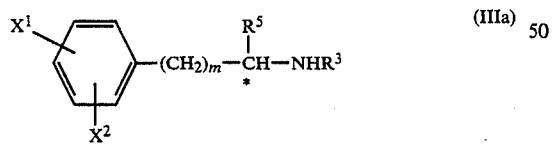 |
| $-CH_2CH_2OC_4H_9-n$ | $-CH_2CH_2OCH_2CH=CH_2$ | |

Formula (VI) provides a general definition of the alkylating agents furthermore to be used as starting substances for the preparation of the new compounds of the formula (II). In this formula (VI), $R^2$ preferably or particularly preferably represents those radicals which have already been mentioned as preferred or particularly preferred for this substituent in connection with the description of the substances of the formula (I) according to the invention. Q in this formula (VI) represents halogen, preferably chlorine, bromine or iodine, or represents the radical $-OSO_2OR^2$, wherein $R^2$ has the above-mentioned meanings.

The compounds of the formula (VI) are generally known compounds of organic chemistry.

Examples which may be mentioned of compounds of the formula (VI) are: methyl chloride, methyl bromide, methyl iodide, ethyl bromide, ethyl iodide, n-propyl bromide, n-propyl iodide, i-propyl bromide, i-propyl iodide, n-butyl bromide, n-butyl iodide, i-butyl bromide, i-butyl iodide, sec.-butyl bromide, sec.-butyl iodide, tert.-butyl bromide and tert.-butyl iodide, as well as dimethyl sulphate, diethyl sulphate and di-n-propyl sulphate.

Formula (III) provides a general definition of the amines also to be used as starting substances in the process according to the invention. In this formula (III), $R^3$, $R^4$, $X^1$, $X^2$ and m preferably or particularly preferably represent those radicals which have already been mentioned as preferred or particularly preferred for these substituents in connection with the description of the substances of the formula (I) according to the invention.

Optically active R- or S-enantiomers of the amines of the formula (IIIa)

$$X^1\text{-Ar}(X^2)-(CH_2)_m-\underset{\underset{*}{\mid}}{CH}(R^5)-NHR^3 \quad (IIIa)$$

in which
$X^1$, $X^2$, $R^3$, $R^5$ and m have the abovementioned meanings,
are used as starting substances in the preparation of optically active R- and S-enantiomers of the 3-amino-2-cyano-acrylic acid esters of the formula (Ib). The optically active S-enantiomers of the amines of the formula (IIIa) are preferably used.

The amines of the formula (III) and (IIIa) are known or can be prepared in a simple manner by processes which are known in principle (compare, for example, Organikum, VEB-Verlag Berlin, page 544 et seq. (1977) and Org. Synthesis, Coll. Volume II, 503 (1943)).

Examples which may be mentioned of the compounds of the formula (III) are:

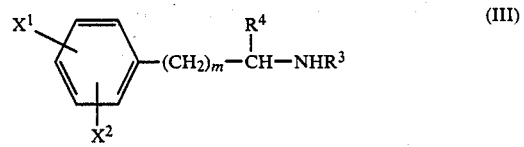

TABLE 4

| $X^1$-Ar($X^2$)- | m | $R^3$ | $R^4$ |
|---|---|---|---|
| phenyl | 0 | H | H |
| phenyl | 0 | H | $CH_3$ |
| phenyl | 0 | $CH_3$ | $CH_3$ |
| phenyl | 0 | $CH_3$ | H |
| phenyl | 1 | H | H |
| phenyl | 1 | H | $CH_3$ |
| phenyl | 1 | $CH_3$ | H |

TABLE 4-continued

| Ar (X¹/X² substituted phenyl) | m | R³ | R⁴ |
|---|---|---|---|
| phenyl | 1 | CH₃ | CH₃ |
| phenyl | 1 | CH₃ | H |
| 3-CF₃-phenyl | 1 | H | CH₃ |
| 2-OCH₃-phenyl | 1 | H | CH₃ |
| 4-H₃CO-phenyl | 1 | H | CH₃ |
| 4-Cl-phenyl | 1 | H | CH₃ |
| 2-F-phenyl | 1 | H | CH₃ |
| 4-F-phenyl | 1 | H | CH₃ |
| 4-biphenyl | 0 | H | CH₃ |
| phenyl | 2 | H | CH₃ |
| phenyl | 3 | H | CH₃ |
| phenyl | 4 | H | CH₃ |
| phenyl | 5 | H | CH₃ |
| 4-Cl-phenyl | 1 | H | H |
| 3-F₃C-phenyl | 1 | H | H |
| phenyl | 0 | H | C₂H₅ |
| phenyl | 0 | H | C₃H₇—n |
| phenyl | 0 | H | C₄H₉—n |
| 4-Cl-phenyl | 0 | H | CH₃ |
| 4-H₅C₂NH-phenyl | 0 | H | CH₃ |
| 4-Br-phenyl | 0 | H | CH₃ |
| 4-F-phenyl | 0 | H | CH₃ |
| 4-O₂N-phenyl | 0 | H | CH₃ |
| 4-H₃CO-phenyl | 0 | H | CH₃ |

TABLE 4-continued

| X¹/X² aryl | m | $R^3$ | $R^4$ |
|---|---|---|---|
| H₃C—C₆H₄— (4-methylphenyl) | 0 | H | $CH_3$ |
| 3-Br—C₆H₄— | 0 | H | $CH_3$ |
| 2-Cl—C₆H₄— | 0 | H | $CH_3$ |
| F—C₆H₄— | 0 | H | $CH_3$ |
| F₃C—C₆H₄— | 0 | H | $CH_3$ |
| 2-naphthyl | 0 | H | $CH_3$ |
| H₃CNH—C₆H₄— | 0 | H | $CH_3$ |
| Cl—C₆H₄— | 0 | H | H |
| F—C₆H₄— | 0 | H | H |
| H₃CO—C₆H₄— | 0 | H | H |
| 3-Cl—C₆H₄— | 0 | H | H |
| H₂N—C₆H₄— | 0 | H | $CH_3$ |
| (H₃C)₂N—CO—NH—C₆H₄— | 0 | H | $CH_3$ |
| t-H₉C₄—CO—NH—C₆H₄— | 0 | H | $CH_3$ |

Examples which may be mentioned of the R- and S-enantiomers of the amines of the formula (IIIa) are:

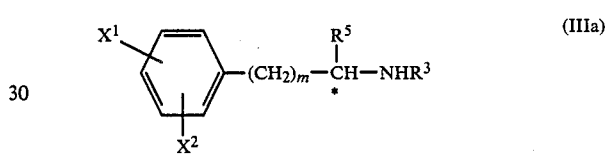

TABLE 5

| X¹/X² aryl | m | $R^3$ | $R^5$ |
|---|---|---|---|
| C₆H₅— | 0 | H | $CH_3$ |
| C₆H₅— | 0 | H | $C_2H_5$ |
| C₆H₅— | 0 | H | $n\text{-}C_3H_7$ |
| C₆H₅— | 0 | H | $i\text{-}C_3H_7$ |
| C₆H₅— | 0 | H | $n\text{-}C_4H_9$ |

TABLE 5-continued

| Ar (X1/X2) | m | R³ | R⁵ |
|---|---|---|---|
| phenyl | 0 | H | i-C₄H₉ |
| 4-Cl-phenyl | 0 | H | CH₃ |
| 4-Br-phenyl | 0 | H | CH₃ |
| 4-F-phenyl | 0 | H | CH₃ |
| 4-H₃CO-phenyl | 0 | H | CH₃ |
| 4-H₃CS-phenyl | 0 | H | CH₃ |
| 4-Cl-phenyl | 1 | H | CH₃ |
| 4-F-phenyl | 1 | H | CH₃ |
| 2-F-phenyl | 1 | H | CH₃ |
| 4-H₃CO-phenyl | 1 | H | CH₃ |
| phenyl | 2 | H | CH₃ |
| phenyl | 3 | H | CH₃ |
| phenyl | 4 | H | CH₃ |
| phenyl | 5 | H | CH₃ |
| phenyl | 0 | CH₃ | CH₃ |
| phenyl | 0 | H | C₂H₅ |
| phenyl | 0 | H | n-C₃H₇ |
| phenyl | 0 | H | i-C₃H₇ |
| 4-Cl-phenyl | 0 | H | C₂H₅ |
| 4-F-phenyl | 0 | H | C₂H₅ |
| 3-F-phenyl | 0 | H | C₂H₅ |
| 2-Br-phenyl | 0 | H | C₂H₅ |
| 4-H₃CO-phenyl | 0 | H | C₂H₅ |
| 4-H₃CS-phenyl | 0 | H | C₂H₅ |

The process according to the invention for the preparation of the new 3-amino-2-cyano-acrylic acid esters of the formula (I) is preferably carried out using diluents. Possible diluents here are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol monoethyl ether, glycol dimethyl ether, diglycol dimethyl ether, tetrahydrofuran and dioxane, alcohols, such as methanol, ethanol, n-propanol or n-butanol, amides, such as, for example, dimethylformamide, and dimethylsulphoxide. The reaction is preferably carried out in the presence of alcohols of the formula $R^1OH$ in order to avoid side reactions.

The reaction temperatures can be varied within a substantial range in the process according to the invention. The reaction is in general carried out at temperatures between 0° C. and 120° C., preferably at temperatures between 15° C. and 80° C.

The process according to the invention is in general carried out under normal pressure. However, it is also possible for it to be carried out under increased or reduced pressure.

For carrying out the process according to the invention, the particular starting substances of the formulae (II) and (III) required are in general employed in approximately equimolar amounts. However, it is also possible for one of the two particular components employed to be used in a relatively large excess. The reactions are in general carried out in a suitable diluent in the presence of an acid acceptor, and the reaction mixture is stirred at the particular required temperature for several hours. Working up in the process according to the invention is in each case carried out by customary methods.

The new compounds are obtained in the form of oils, some of which cannot be distilled without decomposition, but can be freed from the last volatile constituents by so-called "incipient distillation", that is to say by prolonged heating to moderately elevated temperatures under reduced pressure, and can be purified in this manner. The oils which have been subjected to "incipient distillation" can, however, also be taken up in inert solvents, such as, for example, n-hexane or benzine, this mixture can be filtered over a silica gel column and the solvent can then be removed under a waterpump vacuum. They are characterized by their refractive index or $^1$H-NMR spectra.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are particularly suitable for selectively combating mono- and dicotyledon weeds, in particular in monocotyledon crops, by the post-emergence method. The compounds according to the invention exhibit, for example when used by the post-emergence method in wheat, no damage to the crop plants, but a clear activity against weeds such as Chenopodium, Abutilon, Viola, Polygonum, Echinochloa and Setaria.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montomorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, N-(2-benzothiazolyl)-N,N'-dimethylurea, 3-(3-chloro-4-methylphenyl)-1,1-dimethylurea, 3-(4-isopropylphenyl)-1,1-dimethylurea, 2-chloro-N-{[4-methoxy-6-methyl-1,3,5-triazin-2-yl)-amino]-carbonyl}-benzenesulphonamide, 2-ethylamino-6-(1,1-dimethylethylamino)-4-methylthio-1,3,5-triazine, 2-chloro-4-ethylamino-6-(1-methylethyl)-1,3,5-triazine, 2-chloro-4,6-diethylamino-1,3,5-triazine, 2-chloro-4-(1-cyano-1-methylethylamino)-6-ethylamino-1,3,5-triazine, 4-amino-6-(1,1-dimethylethyl)-3-methylthio-1,2,4-triazin-5(4H)-one, 4-amino-6-(1,1-dimethylethyl)-3-ethylthio-1,2,4-triazin-5(4H)-one, 1-amino-6-ethylthio-3-(2,2-dimethylpropyl)-1,3,5-triazine-2,4-(1H,3H)-dione, methyl 3-(2,4-dichlorophenoxy)-6-nitro-benzoate, methyl 2-[4-(2,4-dichlorophenoxy)-phenoxy]-propionate, ethyl 2-{4-[(6-chloro-2-benzoxazolyl)-oxy]-phenoxy}-propionate, the R-enantiomer of (trimethylsily)-methyl 2-{4-[(3,5-dichloro-2-pyridyl)oxy]-phenoxy}-propionate, 2,4-dichlorophenoxyacetic acid, 2-(2,4-dichlorophenoxy)-propionic acid, 4-chloro-2-methylphenoxy-acetic acid, 2-(4-chloro-2-methyl-phenoxy)-propionic acid, 3,5-diiodo-4-hydroxy-benzonitrile, 3,5-dibromo-4-hydroxy-benzonitrile, O-(6-chloro-3-phenylpyridazin-4-yl) S-octyl thiocarbonate [(4-amino-3,5-dichloro-6-fluoro-2-pyridyl)oxy]-acetic acid and 3-isopropyl-2,1,3-benzothiadiazin-4-one 2,2-dioxide. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

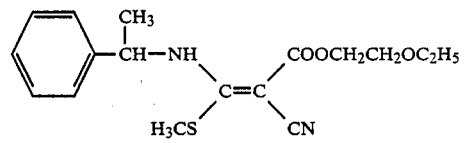

12.1 g (0.1 mol) of 1-phenyl-ethylamine are added dropwise to a solution of 26.1 g (0.1 mol) of 2-(ethoxy)-ethyl 2-cyano-3,3-dimethylthio-acrylate in 150 ml of ethanol so that the internal temperatue does not exceed +35° C. The solvent is then removed. The resulting oily crude product is stirred with n-hexane and purified over a silica gel column.

16.7 g (50% of theory) of 2-(ethoxy)-ethyl 2-cyano-3-methylthio-3-(1-phenyl-ethylamino)-acrylate are thus obtained as a yellow oil.

$^1$H-NMR (CDCl$_3$): δ=5.25 (m, 1H, —CH—N—), 1.6 (d, 3H,

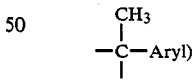

ppm.

Example 2

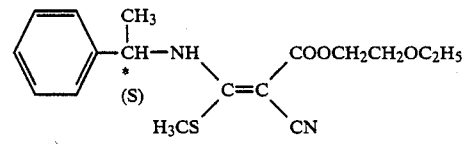

12.1 g (0.1 mol) of (S-)-1-phenyl-ethylamine are added dropwise to a solution of 26.1 g (0.1 mol) of 2-(ethoxy)-ethyl 2-cyano-3,3-dimethylthio-acrylate in 150 ml of ethanol so that the internal temperature does not exceed +35° C. The solvent is then removed. The resulting oily crude product is stirred with n-hexane and purified over a silica gel column.

16.7 g (50% of theory) of 2-(ethoxy)-ethyl (S+)-2-cyano-3-methylthio-3-(1-phenyl-ethylamino)-acrylate are thus obtained as a yellow oil.

Optical rotation: $[\alpha]_D^{28.5} = +192°$ (1 molar solution in chloroform; cell length 10 cm).

The following compounds of the formula (I) can be prepared analogously to Example 1 or 2 and according to the general statements for the preparation:

TABLE 6

$$\begin{array}{c} X^1 \\ \phantom{X} \\ X^2 \end{array}\!\!\!\!\!\!\!\!\!\!\!\!\!\!\!-(CH_2)_m-\underset{R^4}{\overset{R^4}{CH}}-\underset{}{\overset{R^3}{N}}\underset{R^2S}{\overset{}{\diagdown}}C=C\underset{CN}{\overset{COOR^1}{\diagup}}$$ (I)

| Example No. | X¹ / X² (phenyl) | R¹ | R² | R³ | R⁴ | m | Physical Constants ¹H—NMR (CDCl₃)/[ppm.] |
|---|---|---|---|---|---|---|---|
| 3 | 3-H₃CO-phenyl | —CH₂CH₂OC₂H₅ | CH₃ | H | H | 0 | δ = 4.7 (d, 2H, —CH₂—N—) |
| 4## | phenyl | —CH₂CH₂OC₂H₅ | CH₃ | H | CH₃ | 0 | δ = 5.3 (m, 1H, —CH—N—) |
| 5 | phenyl | —CH₂CH₂OC₂H₅ | i-C₃H₇ | H | CH₃ | 0 | δ = 4.0 (m, 1H, —S—CH—) |
| 6## | phenyl | —CH₂CH₂OC₂H₅ | i-C₃H₇ | H | CH₃ | 0 | δ = 4.0 (m, 1H, —S—CH—) |
| 7# | phenyl | —CH₂CH₂OC₂H₅ | i-C₃H₇ | H | CH₃ | 0 | δ = 4.0 (m, 1H, —S—CH—) |
| 8 | phenyl | —CH₂CH₂OC₂H₅ | C₂H₅ | H | CH₃ | 0 | δ = 3.1 (m, 2H, —S—CH₂—) |
| 9## | phenyl | —CH₂CH₂OC₂H₅ | C₂H₅ | H | CH₃ | 0 | δ = 3.1 (m, 2H, —S—CH₂—) |
| 10# | phenyl | —CH₂CH₂OC₂H₅ | C₂H₅ | H | CH₃ | 0 | δ = 3.1 (m, 2H, —S—CH₂—) |
| 11 | 4-Cl-phenyl | —CH₂CH₂OC₂H₅ | CH₃ | H | CH₃ | 0 | δ = 2.6 (s, 3H, —S—CH₃) |

TABLE 6-continued $$\text{(I)}$$

Structure (I):
$$X^1, X^2\text{-substituted phenyl}-(CH_2)_m-CH(R^4)-N(R^3)-C(SR^2)=C(CN)(COOR^1)$$

| Example No. | X¹, X² (phenyl ring) | R¹ | R² | R³ | R⁴ | m | Physical Constants ¹H—NMR (CDCl₃)/[ppm.] |
|---|---|---|---|---|---|---|---|
| 12 | 4-Br-phenyl | —CH₂CH₂OC₂H₅ | CH₃ | H | CH₃ | 0 | δ = 2.6 (s, 3H, —S—CH₃) |
| 13 | 3-H₃CO-phenyl | —CH₂CH₂OC₂H₅ | CH₃ | H | CH₃ | 0 | δ = 10.3 (d, 1H, —NH) |
| 14 | phenyl | —CH₂CH₂OC₂H₅ | CH₃ | CH₃ | H | 0 | δ = 4.9 (s, 2H, —CH₂—N—) |
| 15 | 4-H₃CO-phenyl | —CH₂CH₂OC₂H₅ | CH₃ | H | H | 0 | δ = 3.8 (m, 2H, —CH₂—N—) |
| 16 | 3,4-(H₃CO)₂-phenyl | —CH₂CH₂OC₂H₅ | CH₃ | H | H | 0 | δ = 3.8 (m, 2H, —CH₂—N—) |
| 17 | 4-Cl-phenyl | —CH₂CH₂OC₂H₅ | CH₃ | H | H | 0 | δ = 4.8 (d, 2H, —CH₂—N—) |
| 18 | phenyl | —CH₂CH₂OC₂H₅ | CH₃ | H | H | 1 | δ = 2.9 (t, 2H, —CH₂—Ar) |
| 19 | 4-Cl-phenyl | —CH₂CH₂OC₂H₅ | CH₃ | H | H | 1 | δ = 2.9 (t, 2H, —CH₂—Ar) |
| 20 | phenyl | —CH₂CH₂OC₂H₅ | CH₃ | H | H | 2 | δ = 2.7 (t, 2H, Ar—C—CH₂—) |
| 21 | phenyl | —CH₂CH₂OC₂H₅ | CH₃ | H | CH₃ | 2 | δ = 2.6 (m, 2H, Ar—C—CH₂—) |

TABLE 6-continued $$\text{(I)} \quad X^1\text{-}\underset{X^2}{\underset{|}{C_6H_3}}\text{-}(CH_2)_m\text{-}\underset{R^4}{\underset{|}{CH}}\text{-}\underset{R^3}{\underset{|}{N}}\text{-}\underset{R^2S}{\underset{|}{C}}=\underset{CN}{\underset{|}{C}}\text{-}COOR^1$$

| Example No. | X¹/X² (aryl) | R¹ | R² | R³ | R⁴ | m | Physical Constants $^1$H—NMR (CDCl$_3$)/[ppm.] |
|---|---|---|---|---|---|---|---|
| 22 | phenyl | —CH$_2$CH$_2$OC$_2$H$_5$ | CH$_3$ | H | H | 3 | δ = 1.7 (m, 2H, —CH$_2$—C—N—) |
| 23 | phenyl | —CH$_2$CH$_2$OC$_3$H$_7$—i | CH$_3$ | H | CH$_3$ | 0 | δ = 2.6 (s, 3H, —SCH$_3$) |
| 24# | phenyl | —CH$_2$CH$_2$OC$_3$H$_7$—i | CH$_3$ | H | CH$_3$ | 0 | δ = 2.6 (s, 3H, —SCH$_3$) |
| 25## | phenyl | —CH$_2$CH$_2$OC$_3$H$_7$—i | CH$_3$ | H | CH$_3$ | 0 | δ = 2.6 (s, 3H, —SCH$_3$) |
| 26 | phenyl | —CH$_2$CH$_2$OCH$_2$—phenyl | CH$_3$ | H | CH$_3$ | 0 | δ = 3.7 (q, 2H, —OCH$_2$—C—) |
| 27# | phenyl | —CH$_2$CH$_2$OCH$_2$—phenyl | CH$_3$ | H | CH$_3$ | 0 | δ = 3.7 (q, 2H, —OCH$_2$—C—) |
| 28 | 4-F-phenyl | —CH$_2$CH$_2$OC$_2$H$_5$ | CH$_3$ | H | CH$_3$ | 0 | δ = 5.3 (quint, 1H, Ar—CH—) |
| 29 | 4-F-phenyl | —CH$_2$CH$_2$OC$_2$H$_5$ | CH$_3$ | H | H | 0 | δ = 4.8 (d, 2H, —CH$_2$—N—) |
| 30 | 4-O$_2$N-phenyl | —CH$_2$CH$_2$OC$_2$H$_5$ | CH$_3$ | H | H | 0 | δ = 2.6 (s, 3H, —SCH$_3$) |
| 31 | 4-H$_3$C-phenyl | —CH$_2$CH$_2$OC$_2$H$_5$ | CH$_3$ | H | CH$_3$ | 0 | δ = 2.6 (s, 3H, —SCH$_3$) |
| 32 | 4-F$_3$C-phenyl | —CH$_2$CH$_2$OC$_2$H$_5$ | CH$_3$ | H | H | 0 | δ = 4.9 (d, 2H, —CH—N—) |

TABLE 6-continued $$\text{(I)}\quad \underset{X^2}{\overset{X^1}{\bigcirc}}-(CH_2)_m-\underset{\underset{H}{|}}{\overset{R^4}{C}}\underset{\underset{R^2S}{|}}{\overset{R^3}{N}}-\underset{\underset{CN}{|}}{\overset{COOR^1}{C}}=C$$

| Example No. | X¹ / X² (phenyl substitution) | R¹ | R² | R³ | R⁴ | m | Physical Constants ¹H—NMR (CDCl₃)/[ppm.] |
|---|---|---|---|---|---|---|---|
| 33## | 4-Br-C₆H₄ | —CH₂CH₂OC₂H₅ | CH₃ | H | CH₃ | 0 | δ = 2.6 (s, 3H, —S—CH₃) |
| 34 | 4-(H₅C₂NH)-C₆H₄ | —CH₂CH₂OC₂H₅ | CH₃ | H | CH₃ | 0 | δ = 5.3 (quint, 1H, —CH—N—) |
| 35 | C₆H₅ | —CH₂CH₂OC₂H₅ | CH₃ | H | n-C₄H₉ | 0 | δ = 1.9 (m, 2H, —C—CH₂—C—) |
| 36 | 4-Cl-C₆H₄ | —CH₂CH₂OC₂H₅ | CH₃ | H | H | 1 | δ = 4.3 (t, 2H, —CH₂—N—) |
| 37 | 4-F₃C-C₆H₄ | —CH₂CH₂OC₂H₅ | CH₃ | H | CH₃ | 1 | δ = 2.7 (t, 2H, —CH₂—N—) |
| 38 | 2-OCH₃-C₆H₄ | —CH₂CH₂OC₂H₅ | CH₃ | H | H | 0 | δ = 4.8 (d, 2H, —CH₂—N—) |
| 39 | 3-H₃CO-C₆H₄ | —CH₂CH₂OC₂H₅ | CH₃ | H | H | 1 | δ = 3.8 (m, 2H, Ar—CH₂—) |
| 40 | 2-F-C₆H₄ | —CH₂CH₂OC₂H₅ | CH₃ | H | H | 0 | δ = 4.8 (d, 2H, —CH₂—N—) |
| 41 | 2-F-C₆H₄ | —CH₂CH₂OC₂H₅ | CH₃ | H | CH₃ | 0 | δ = 2.6 (s, 3H, —SCH₃) |
| 42 | 3-Br-C₆H₄ | —CH₂CH₂OC₂H₅ | CH₃ | H | CH₃ | 0 | δ = 1.6 (d, 3H, —C—CH₃) |

TABLE 6-continued $$\text{(I)}$$

Structure (I): X¹ and X² substituted phenyl—(CH₂)ₘ—CH(R⁴)—N(R³)—C(SR²)=C(CN)(COOR¹)

| Example No. | X¹/X² (aryl group) | R¹ | R² | R³ | R⁴ | m | Physical Constants ¹H—NMR (CDCl₃)/[ppm.] |
|---|---|---|---|---|---|---|---|
| 43 | 4-biphenylyl | —CH₂CH₂OC₂H₅ | CH₃ | H | CH₃ | 0 | δ = 2.6 (s, 3H, —SCH₃) |
| 44 | 2-naphthyl | —CH₂CH₂OC₂H₅ | CH₃ | H | CH₃ | 0 | δ = 2.6 (s, 3H, —SCH₃) |
| 45 | phenyl | —CH₂CH₂OC₂H₅ | CH₃ | H | CH₃ | 1 | δ = 2.8 (s, 1H, —N—CH₃) |
| 46 | 2-methoxyphenyl | —CH₂CH₂OC₂H₅ | CH₃ | H | H | 1 | δ = 10.1 (m, 1H, —NH) |
| 47 | 4-bromophenyl | —CH₂CH₂OC₂H₅ | CH₃ | H | H | 1 | δ = 3.9 (q, 2H, —CH₂—N—) |
| 48 | 2-chlorophenyl | —CH₂CH₂OC₂H₅ | CH₃ | H | H | 0 | δ = 4.5 (d, 2H, —CH₂—N—) |
| 49 | phenyl | —CH₂CH₂OC₂H₅ | CH₃ | H | H | 0 | δ = 2.6 (s, 3H, —SCH₃) |
| 50 | 3,4-dichlorophenyl | —CH₂CH₂OC₂H₅ | CH₃ | H | H | 0 | δ = 4.7 (d, 2H, —CH₂—N—) |
| 51 | 4-bromophenyl | —CH₂CH₂OC₂H₅ | CH₃ | H | H | 0 | δ = 4.7 (d, 2H, —CH₂—N—) |
| 52 | 2,4-dimethoxyphenyl | —CH₂CH₂OC₂H₅ | CH₃ | H | H | 0 | δ = 4.6 (d, 2H, —CH₂—N—) |

TABLE 6-continued $$\text{X}^1\text{-C}_6\text{H}_3(\text{X}^2)-(\text{CH}_2)_m-\text{CH}(\text{R}^4)-\text{N}(\text{R}^3)-\text{C}(\text{SR}^2)=\text{C}(\text{COOR}^1)(\text{CN})$$ (I)

| Example No. | $X^1$ / $X^2$ | $R^1$ | $R^2$ | $R^3$ | $R^4$ | m | Physical Constants $^1$H—NMR (CDCl$_3$)/[ppm.] |
|---|---|---|---|---|---|---|---|
| 53 |  Cl, Cl | —CH$_2$CH$_2$OC$_2$H$_5$ | CH$_3$ | H | H | 0 | δ = 4.9 (d, 2H, —CH$_2$—N—) |
| 54 |  F | —CH$_2$CH$_2$OC$_2$H$_5$ | CH$_3$ | H | H | 1 | δ = 10.1 (m, 1H, —NH) |

Note:
\# = the optically active S—enantiomeric derivative
\#\# = the optically active R—enantiomeric derivative

Example 5 A

The structural isomer of Example 5.
$^1$H-NMR (CDCl$_3$): δ=9.65 (d, 1H,

—NH), 4.8 (q, 1H,

—CH—N—), 4.5 (m, 1H,

—S—CH—)

ppm.

Example 6 A

The structural isomer of Example 6.
$^1$H-NMR (CDCl$_3$): δ=9.65 (d, 1H,

—NH), 4.8 (q, 1H,

—CH—N—), 4.5 (m, 1H,

—S—CH—)

30 ppm.

Example 7 A

The structural isomer of Example 7.
$^1$H-NMR (CDCl$_3$): δ=9.65 (d, 1H,

—NH), 4.8 (q, 1H,

—CH—N—), 4.5 (m, 1H,

—S—CH—)

ppm.

STARTING COMPOUNDS OF THE FORMULA (V)

Example (V-1)

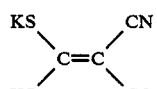

470 g (4 mols) of 95% pure potassium tert.-butanolate are added to a solution of 314 g (2 mols) of 2-(ethoxy)-ethyl 2-cyanoacetate and 152 g (2 mols) of carbon disulphide in 3 l of ether (absolute) at 10° C. When the addition has ended, the reaction mixture is stirred at 20° C. for a further 30 minutes. The dipotassium salt of the above structural formula is filtered off with suction and used without further purification for the preparation of the compounds of the formula (II).

The following compounds of the formula (V) can be prepared analogously to Example (V-1):

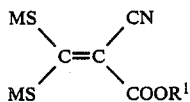

TABLE 7

| Ex. | M | $R^1$ |
|---|---|---|
| (V-2) | K | $-CH_2CH_2OCH_3$ |
| (V-3) | K | $-CH_2CH_2OC_3H_7-n$ |
| (V-4) | K | $-CH_2CH_2OC_3H_7-i$ |

(V-5) K 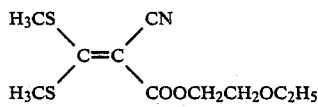

STARTING COMPOUNDS OF THE FORMULA (II)

Example (II-1)

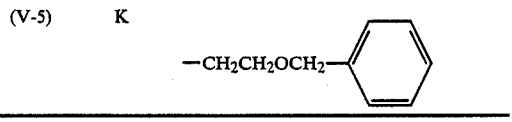

The dipotassium salt of Example (V-1) is dissolved in 2,000 ml of water and reacted dropwise with 504 g (4 mols) of dimethyl sulphate at an internal temperature of 20° C., with cooling. When the addition has ended, the mixture is subsequently stirred at 20° C. for half an hour. The aqueous phase is separated off and the organic phase is taken up in 2,000 ml of ether. The ether phase is washed four times with 1,000 ml of water each time, dried over sodium sulphate and concentrated. The residue is taken up in n-hexane and purified over a silica gel column. However, the crude product can also be used without further purification.

222 g (85% of theory) of 2-(ethoxy)-ethyl 2-cyano-3,3-dimethylthio-acrylate are thus obtained as a yellow oil.

$^1$H-NMR (CDCl$_3$): δ=4.4 (m, 2H, —COOCH$_2$—), 1.2 (t, 3H,

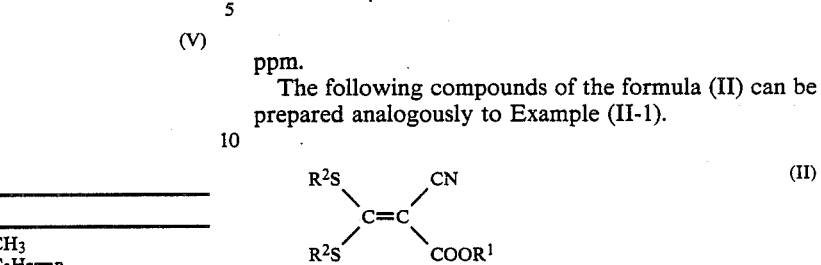

ppm.

The following compounds of the formula (II) can be prepared analogously to Example (II-1).

TABLE 8

| Example No. | $R^1$ | $R^2$ | Constant constants $^1$H—NMR (CDCl$_3$)/[ppm.] |
|---|---|---|---|
| II-2 | $-CH_2CH_2OC_2H_5$ | $-C_2H_5$ | δ = 3.1 (m, 4H, —S—CH$_2$—) |
| II-3 | $-CH_2CH_2OC_2H_5$ | $-C_3H_7-i$ | δ = 1.4 (m, 12H, —S(CH$_3$)$_2$) |
| II-4 | $-CH_2CH_2OC_2H_5$ | $-C_4H_9-i$ | |
| II-5 | $-CH_2CH_2OC_2H_5$ | $-CH_2CH=CH_2$ | |
| II-6 | $-CH_2CH_2OCH_2-\text{Ph}$ | $-CH_3$ | |

Example A

Post-emergence test/Greenhouse

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the compounds of preparation examples (1) and (2) exhibit a considerably better activity, coupled with complete tolerance in wheat, against mono- and dicotyledon weeds such as, for example, Abutilon, Viola, Echinochloa and the like than comparison substance (A).

It will be understood that the specification and examples are illustrative but not limitative of the present invention and that other embodiments within the spirit and scope of the invention will suggest themselves to those skilled in the art.

We claim:

1. A 3-amino-2-cyanoacrylic acid ester of the formula

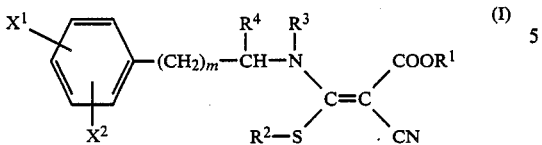

in which
- $R^1$ represents alkoxyalkyl with in each case 1 to 6 carbons atoms in the individual alkyl parts, or represents benzyloxyalkyl with 1 to 6 carbon atoms in the alkyl part,
- $R^2$ represents alkyl with 1 to 6 carbon atoms, or represents alkenyl with 3 to 8 carbon atoms,
- $R^3$ represents hydrogen or alkyl with 1 to 6 carbon atoms,
- $R^4$ represents hydrogen, or represents alkyl which has 1 to 6 carbon atoms and is optionally substituted by hydroxyl, fluorine, chlorine, $C_1$–$C_4$-alkoxy or di-$C_1$–$C_4$-alkylamino,
- $X^1$ and $X^2$ are identical or different and represent hydrogen, fluorine, chlorine, bromine, nitro, $C_1$–$C_4$-alkyl, $C_1$–$C_4$-alkoxy, $C_1$–$C_4$-alkylthio, halogeno-$C_1$–$C_4$-alkyl, halogeno-$C_1$–$C_4$-alkoxy, amino, $C_1$–$C_4$-alkylamino, $C_1$–$C_4$ alkylcarbonylamino, N-$C_1$–$C_4$-alkyl-carbonyl-N-$C_1$–$C_4$-alkylamino, di-$C_1$–$C_4$-alkylamino-carbonyl-amino or represent aryl or aryloxy which have 6 to 10 carbon atoms in the aryl part and are optionally monosubstituted, disubstituted or trisubstituted by identical or different substituents from the group comprising halogen, nitro, cyano, $C_1$–$C_2$-alkyl, $C_1$–$C_2$-alkoxy, $C_1$–$C_2$-alkylthio, trifluoromethyl, trifluoroethoxy and trifluoromethylthio or
- $X^1$ and $X^2$ together with the adjacent phenyl radical represent naphthyl, and
- m represents the number 0, 1, 2, 3, 4 or 5.

2. A 3-amino-2-cyanoacrylic acid ester according to claim 1 in which
- $R^1$ represents alkoxyalkyl with in each case 1 to 4 carbon atoms in the individual alkyl parts or represents benzyloxyalkyl with 1 to 4 carbon atoms in the alkyl part,
- $R^2$ represents alkyl with 1 to 4 carbon atoms or alkenyl with 3 to 6 carbon atoms,
- $R^3$ represents hydrogen or alkyl with 1 to 4 carbon atoms,
- $R^4$ represents hydrogen, or represents alkyl which has 1 to 4 carbon atoms and is optionally substituted by hydroxyl, fluorine, chlorine, methoxy, ethoxy, dimethylamio or diethylamino,
- $X^1$ and $X^2$ are identical or different and represent hydrogen, fluorine, chlorine, bromine, nitro, methy, ethyl, methoxy, ethoxy, methylthio, ethylthio, trifluoromethyl, trifluoromethoxy, amino, methylamino, ethylamino, n-propylamino, i-propylamino, n-butylamino, tert.-butylamino, methylcarbonylamino, ethylcarbonylamino, n-propylcarbonylamino, i-propylcarbonylamino, n-butylcarbonylamino, i-butylcarbonylamino, tert.-butylcarbonylamino, N-methylcarbonyl-N-methylamino, N-ethylcarbonyl-N-methylamino, N-n-propylcarbonyl-N-methylamino, N-i-propylcarbonyl-N-methylamino or represent phenyl or phenoxy which are optionally monosubstituted or disubstituted by identical or different substituents from the group comprising fluorine, chlorine, nitro, cyano, methyl, ethyl, methoxy, ethoxy, methylthio, ethylthio, trifluoromethyl, trifluoromethoxy and trifluoromethylthio, or
- $X^1$ and $X^2$ together with the adjacent phenyl radical represent naphthyl and
- m represents the number 0, 1 or 2.

3. A 3-amino-2-cyanoacrylic acid ester according to claim 1, in which $R^4$ is alkyl has 1 to 6 carbon atoms and is optionally substituted by hydroxyl, fluorine, chlorine, $C_1$–$C_4$-alkoxy or di-$C_1$–$C_4$-alkylamino in substantially pure R or S enantiomeric configuration.

4. A compound according to claim 1, wherein such compound is 2-(ethoxy)-ethyl-2-cyano-3-methylthio-3-(1-phenyl-ethylamino)-acrylate of the formula

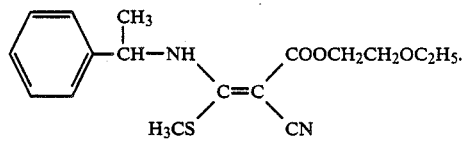

5. A compound according to claim 4 in S enantiomeric form.

6. A compound according to claim 1, wherein such compound is 2-(ethoxy)-ethyl-2-cyano-3-methylthio-3-(1-p-chlorophenylethylamino)-acrylate of the formula

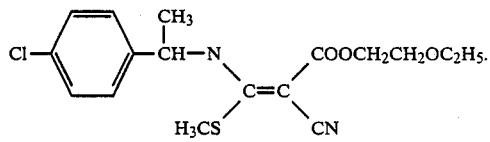

7. A compound according to claim 1, wherein such compound is 2-(ethoxy)-ethyl-2-cyano-3-methylthio-3-(p-trifluoromethylphenyl-methylamino)-acrylate of the formula

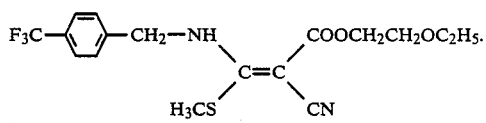

8. A compound according to claim 1, wherein such compound is 2-(ethoxy)-ethyl-2-cyano-3-methylthio-3-(1-p-bromophenylethylamino)-acrylate of the formula

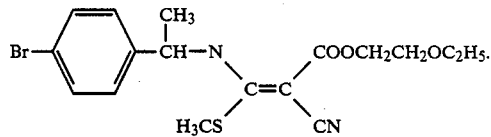

9. A compound according to claim 8 in R enantiomeric form.

10. A herbicidal composition comprising a herbicidally effective amount of a compound according to claim 1 and a diluent.

11. A method of combating unwanted vegetation which comprises applying to such vegetation or to a locus from which it is desired to exclude such vegetation a herbicidally effective amount of a compound according to claim 1.

12. The method according to claim 11, wherein such compound is
2-(ethoxy)-ethyl-2-cyano-3-methylthio-3-(1-phenylethylamino)-acrylate,
2-(ethoxy)-ethyl-2-cyano-3-methylthio-3-(1-p-chlorophenyl-ethylamino)-acrylate,
2-(ethoxy)-ethyl-2-cyano-3-methylthio-3-(p-trifluoromethylphenyl-methylamino)-acrylate or
2-(ethoxy)-ethyl-2-cyano-3-methylthio-3-(1-p-bromophenyl-ethylamino)-acrylate.

* * * * *